United States Patent [19]

Iofis et al.

[11] Patent Number: 4,713,071
[45] Date of Patent: Dec. 15, 1987

[54] HEART VALVE PROSTHESIS

[76] Inventors: Naum A. Iofis, Lomonosovsky prospekt, 23, kv. 416; Rudolf N. Vettsel, ulitsa Vinokurova, 24, korpus 4, kv. 63; Alexandr S. Bukatov, ploschad Pobedy, 1, korpus "A", kv. 122; Semen G. Khurtsilava, ulitsa Kedrova, 5, kv. 118, all of, Moscow, U.S.S.R.

[21] Appl. No.: 906,623

[22] Filed: Sep. 10, 1986

Related U.S. Application Data

[63] Continuation of Ser. No. 969,424, Jan. 30, 1985, abandoned.

[30] Foreign Application Priority Data

Feb. 16, 1984 [SU] U.S.S.R. ............... 3700753

[51] Int. Cl.⁴ ............................... H61F 2/24
[52] U.S. Cl. ............................... 623/2
[58] Field of Search ............................... 623/2

[56] References Cited

U.S. PATENT DOCUMENTS 3,824,629  7/1974  Shiley ............... 3/1.3
4,057,857  11/1977  Fettel ............... 3/1.5
4,416,029  11/1983  Kaster ............... 137/527 X Primary Examiner—Richard J. Apley
Assistant Examiner—Alan W. Cannon
Attorney, Agent, or Firm—Fleit, Jacobson, Cohn & Price

[57] ABSTRACT

A heart valve prosthesis comprises a valve ring having an opening for the flow of blood, a valve poppet floatingly mounted during opening and closing. For floatingly containing the poppet, and there is provided a single upper support and a lower support structure. The upper support has a flat portion supporting the poppet that bears thereagainst with a depression made in the top side of the poppet. The lower support structure has tabs for supporting the poppet so that the poppet is in the surface-to-the surface contact with the upper support and tabs of the lower support structure when the poppet is in the open position.

7 Claims, 6 Drawing Figures

HEART VALVE PROSTHESIS

This application is a continuation of application Ser. No. 696,424, filed Jan. 30, 1985, now abandoned.

FIELD OF THE ART

The invention relates to the field of medicine and, more specifically, deals with a heart valve prosthesis designed for installation to replace an affected natural heart valve.

PRIOR ART

Known in the art is a heart valve prosthesis comprising a valve ring with an opening for the flow of blood. A poppet for opening and closing the valve opening during operation of the valve is mounted in the opening of the valve ring. The poppet is floatingly contained by means of an upper support and a lower support structure. The lower support structure is usually made in the form of two curved struts having a profiled top side corresponding to the profile of the bottom side of the poppet so as to ensure surface-to-surface contact. The upper support structure is either in the form of a radially extending member received in a respective depression in the top side of the poppet, or comprises a bracket also received in a groove in the top side of the poppet (cf., U.S. Pat. No. 3,824,629, July 23, 1974).

While this known heart valve has certain advantages, e.g., of ensuring surface-to-surface contact between the poppet when closed and the support members, it is deficient in the fact that there is a point contact when the poppet is in the open position. This point contact negatively affects wear resistance, and hence the service life of the prosthesis.

It is an object of the invention to provide a heart valve prosthesis which has the poppet support structures so constructed as to ensure surface contact therebetween of the poppet in its open position, thus enhancing a prolonged service life and improved reliability in operation.

These and other objects are accomplished by a hear valve prosthesis comprising a valve ring having an opening therein for the flow of blood, a valve poppet and a means for floatingly containing the poppet during closing and opening, said means comprising an upper support mounted on a radial holder and a lower support structure. According to the invention, the upper support has a flat portion inclined with respect to a diametrical horizontal plane of the valve ring at an angle corresponding to the angle of inclination of the valve poppet with respect to the same plane when the poppet is in the open position. The lower support structure has profiled portions extending transversely with respect to the radial holder, the configuration of the profiled portions corresponding to the profile of the bottom side of the poppet. The profiled portions are spaced apart from each other and an inclined portion extends in the space therebetween looking in the plan view.

The advantage of such a construction of the heart valve prosthesis resides in the fact that when the valve poppet is in the open position, it is supported by three surfaces, namely by the flat portion of the upper support and two profiled portions on the lower support structure. As a result, the support force in the open position of the valve poppet is distributed over a comparatively larger contact area of the support surface thus, naturally, lowering the specific pressure per unit of area to reduce wear and prolong service life of the valve.

In the case where the lower support structure is in the form of two curved struts extending between the periphery and center of the valve ring, it is preferred to provide the profiled portions on bent-away portions of the struts facing toward each other or bent away in opposite directions, but at any rate transversely with respect to the radial holder of the upper support. To improve conditions for the flow of blood through the valve opening, it is preferred that the lower support structure be made in the form of tabs secured in the valve ring, to the inner periphery thereof, the tabs having a profiled portion so as to lower resistance to the flow in the central zone of the valve ring opening.

The flat portion is preferably inclined at a small acute angle of, e.g., 1°–3° with respect to a plane drawn at right angles with respect to the plane of the radial holder. This facility enables additional rotation of the valve poppet in accordance with the dynamics of the blood flow.

The invention will now be described with reference to specific non-limiting embodiments thereof, illustrated in the accompanying drawings, in which.

Figure 1:
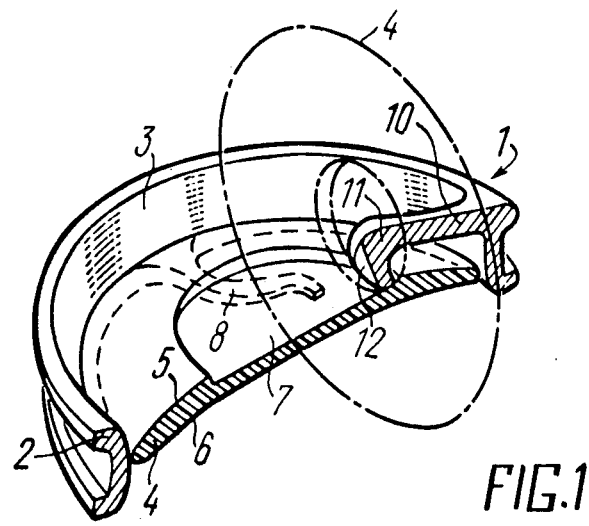
FIG. 1 shows a perspective view, partially in section, of a heart valve prosthesis according to the invention with the poppet shown in the closed and open positions with solid and dotted lines, respectively.
Figure 2:
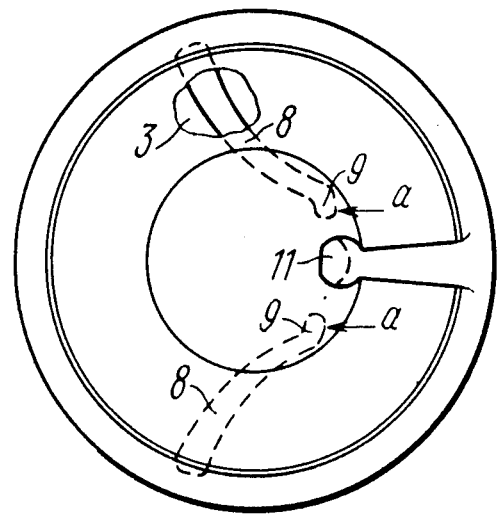
FIG. 2 is a plan view, partially in section, of the heart valve prosthesis shown in FIG. 1.

Referring first to FIG. 1, reference 1 shows a heart valve prosthesis according to the invention in general. The heart valve prosthesis is made of biologically inert materials and comprises a valve ring or body 2 in the form of a cylinder having shoulders designed for mounting a collar (not shown in the drawing for the sake of clarity as it does not have any bearing on this particular invention). The construction, shape and material of such a collar are well known to those skilled in the art. The collar is designed for securing the prosthesis proper to the surrounding tissues during implantation of the prosthesis. The valve ring 2 defines a valve opening 3 and a seat for a valve poppet 4. The valve poppet 4 has top and bottom sides 5 and 6. A depression or recess 7 is made in the top side 5. The poppet 4 can take a closed position in which the poppet is shown with a solid line, or an open position, in which the poppet is shown with dotted lines. In order to floatingly contain the poppet in the valve ring opening during closing and opening, there are provided a lower support structure and a single upper support which are disposed on either side of the poppet 4. The lower support structure is made in the form of two curved struts 8 which are secured, e.g. by welding, to the valve ring 2 and which extend toward the center of the valve ring as can be seen clearly in FIG. 2. The surfaces of the struts facing toward the bottom side of the poppet 4 have a profile corresponding to the profile of this side to ensure surface-to-surface contact therewith when the poppet is in the closed position. As it can be seen in FIG. 2, the distal ends of the struts are bent away toward each other so as to define short tabs 9 spaced apart from each other, the poppet 4 bearing against the tabs when in the open position. Consequently, the tabs 9 have a profile on the side shown by arrows "a" corresponding to the profile of the bottom side 6 of the poppet 4 so as to ensure surface-to-surface contact therewith when the poppet is in the open position. The upper support comprises a radially extending holder 10 in the form of a strut having a spherical support (11) which extends in the space between the tabs 9 looking in the plan view and which is received in the depression 7. The support 11 has a flat surface portion 12 as can be best seen in FIG. 1, which is inclined with respect to a horizontal diametrical plane of the valve ring at an angle corresponding to the angle of inclination of the poppet with respect to the same plane when the poppet is in the open position. As can be seen in FIG. 1, when the poppet 4 is in the open position, the poppet bears with its depression bottom against the flat portion 12, whereby surface-to-surface contact is ensured between the poppet 4 and the support 11.

We do not discuss operation of the above-described heart valve prosthesis in detail since it does not differ in general from a number of other prostheses disclosed in a number of patents, e.g. in U.S. Pat. No. 3,824,629 which is incorporated by reference in this specification. It should be borne in mind that as distinguished from the prior art heart valve prosthesis, the poppet is in surface-to-surface contact with both the support 11 and tabs 9 in the open position of the poppet which, naturally, will lower the force per unit of area and improve wear resistance of the poppet, thus prolonging its service life and enhancing reliability in operation.

Figure 6:
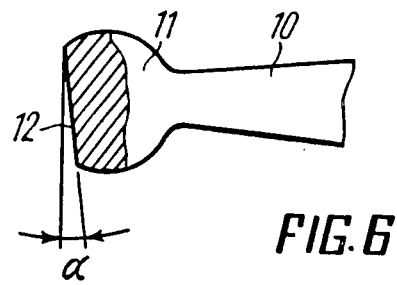
FIG. 6 is an enlarged view of the upper support showing the position of a flat portion thereof.

One possible embodiment of a heart valve prosthesis is described above, but its functional reliability may be further improved by adding certain modifications, taking into account hemodynamics of the flow through the valve opening. It is known that the flow of blood through the valve opening has a slight angular motion component. Consequently, it is preferred to provide for rotation of the poppet 4 out of its plane using for that purpose the above-described flat portion 12. This rotary motion is achieved by inclining the flat portion 12 at an angle α from 1° to 3° with respect to a plane drawn at right angles to the radial holder 10, as shown in FIG. 6, thus providing for said desired rotation.

Figure 3:
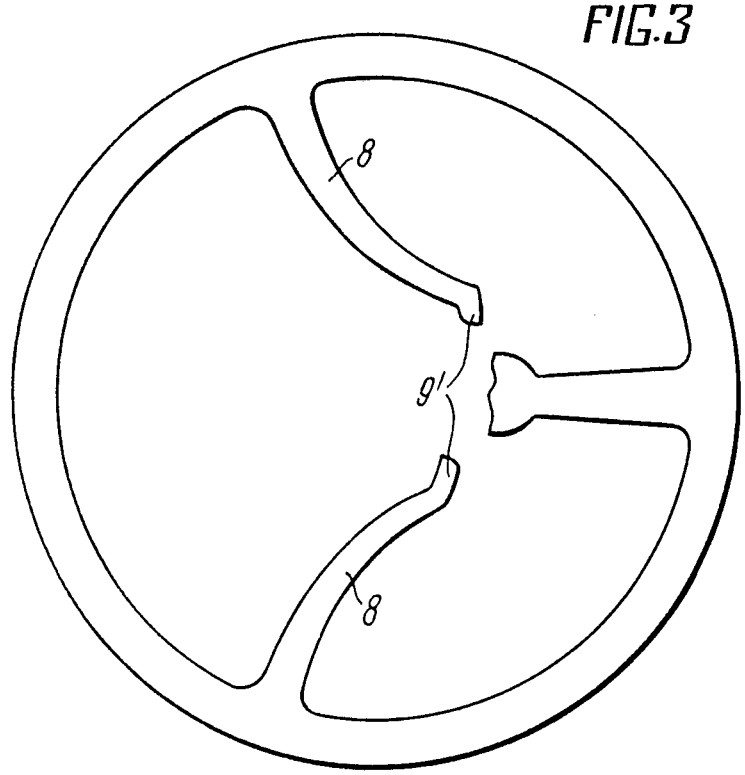
FIG. 3 is an enlarged view of another embodiment of the lower support structure.

In the embodiment shown in FIG. 3, the heart valve prosthesis has the struts 8 and tabs 9' of different length which, in combination with the position of the flat portion 12, enables a better conformity to hemodynamics of the flow.

Figure 5:
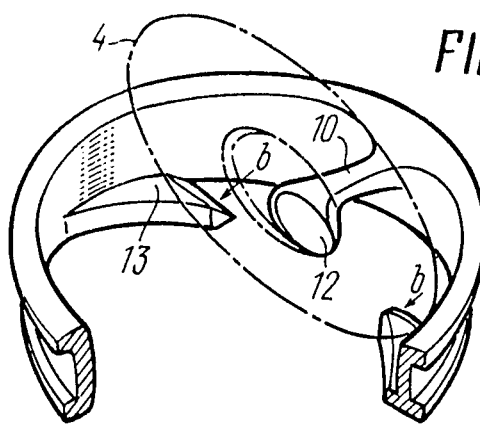
FIG. 5 is still another embodiment of a heart valve prosthesis with a modified lower support structure.
Figure 4:
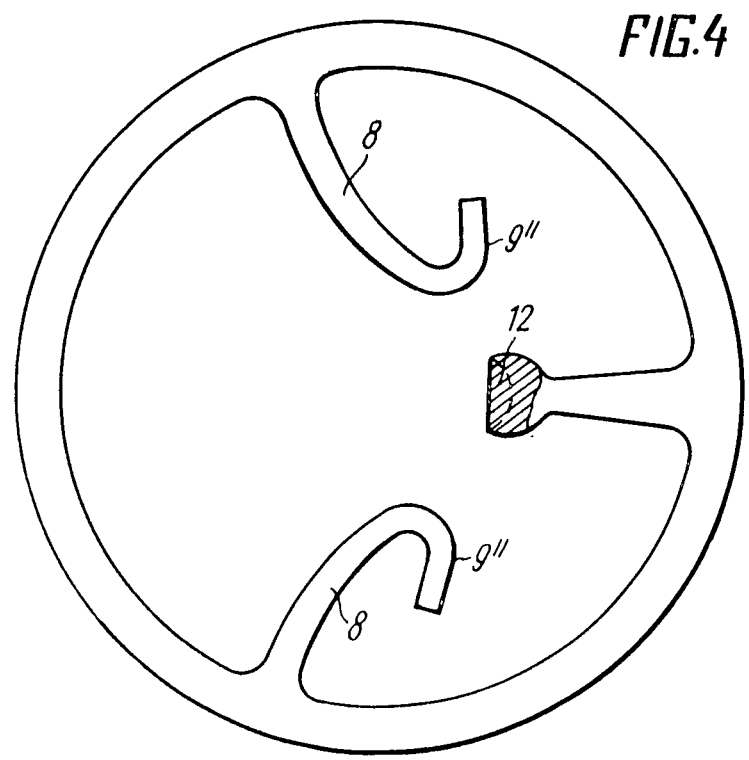
FIG. 4 is a plan view showing the upper support and the lower support structure with another relative position of the profiled portions.

In the embodiment shown in FIG. 3, the tabs 9' of the heart valve prosthesis have been bent away to face toward each other. However, an embodiment shown in FIG. 4 may also be used, wherein the tabs 9" face in opposite directions. two tabs 13 secured directly within the body of the valve ring as shown in FIG. 5, the tabs extending transversely with respect to the radial holder 10 and having on their sides shown by arrows "b" profiles corresponding to the profile of the bottom side of the poppet 4. As can be seen in FIG. 5, these tabs have different length so as to improve hemodynamics of flow.

Therefore, the heart valve prosthesis according to the invention ensures a prolonged service life owing to lower specific loads acting upon its poppet when the poppet is in the open position, and also provides for a stable rotation of the poppet so as to ensure optimum geometry of the flow of blood through the valve.

What is claimed is:

1. A heart valve prosthesis comprising: a valve ring having an opening therein for the flow of blood, a valve poppet having a top side and a bottom side and a concentric depression in the top side thereof, said concentric depression including a surface portion, containing means for floatingly containing the poppet during opening and closing, said containing means being formed by a lower support structure for holding the bottom side of the poppet during closing and by a single upper support and stop member for engaging the top side of the poppet within the depression thereof, said upper support and stop member being mounted on a radial holder extending from said valve ring, said upper support having an inclined surface portion with a surface area which corresponds in surface configuration with and is in surface area contact with said surface portion of said concentric depression when said valve poppet is in an open position to permit blood to pass through said ring opening and is inclined with respect to a horizontal diametrical plane of the valve ring at an angle corresponding to the angle of inclination of the valve poppet with respect to the same plane when the poppet is in the open position to thereby define a stop, and said lower support structure having profiled end portions extending transversely with respect to said radial holder, the profiles of said end portions defining pivot surfaces for the poppet and corresponding to the profile of adjacent portions of the bottom side of the poppet on the sides of said end portions facing toward the holder for engaging the bottom side of the poppet with surface area contact in the open position of the poppet, the end portions of said lower support structure being spaced apart from each other with a clearance space therebetween, and the inclined surface portion of said upper support facing the space between the profiled end portions of said lower support structure, the surface area contact of the poppet with said surface portion of the upper support and said pivot surfaces of the lower support structure in the open position distributing support forces over said surface areas to reduce wear and prolong service life of the prosthesis.

2. A prosthesis according to claim 1, wherein the lower support structure is formed by two struts extending inwardly from the periphery of the ring, the profiled portions of the lower support structure extending transversely with respect to the radial holder and formed by tabs at distal ends of the struts of the lower support structure.

3. A prosthesis according to claim 2, wherein the tabs extend toward each other.

4. A prosthesis according to claim 2, wherein the tabs extend in opposite directions from each other.

5. A prosthesis according to claim 1, wherein the lower support structure is formed by two tabs secured to and extending inwardly of the valve ring, the tabs having profiled surfaces facing toward the bottom side of the poppet for surface engagement therewith and facing toward the holder.

6. A heart valve prosthesis according to claim 1, wherein the flat portion of the upper support is additionally inclined at an acute angle with respect to a plane drawn at right angles with respect to the plane of the radial holder of the upper support.

7. A prosthesis according to claim 6, wherein the angle of inclination of said acute angle is from 1° to 3°.

* * * * *